United States Patent
Diamond

Patent Number: 5,511,563
Date of Patent: *Apr. 30, 1996

[54] APPARATUS AND METHOD FOR TREATING RHEUMATOID AND PSORIATIC ARTHRITIS

[76] Inventor: Donald A. Diamond, 5416 Harbor Rd., Bradenton, Fla. 34209-1832

[*] Notice: The term of this patent shall not extend beyond the expiration date of Pat. No. 5,337,741.

[21] Appl. No.: 198,297

[22] Filed: Feb. 18, 1994

Related U.S. Application Data

[63] Continuation-in-part of Ser. No. 718,615, Jun. 21, 1991, Pat. No. 5,337,741.

[51] Int. Cl.$^6$ ........................................... A61N 5/06
[52] U.S. Cl. ...................... 128/848; 606/3; 606/2; 607/88
[58] Field of Search ................. 606/2, 3, 9, 10, 606/11, 12, 13, 16, 17, 18; 128/898; 607/88, 89

[56] References Cited

U.S. PATENT DOCUMENTS

| | | |
|---|---|---|
| 4,232,678 | 11/1980 | Skovajsa . |
| 4,742,235 | 5/1988 | Koji . |
| 4,836,203 | 6/1989 | Müller et al. .................... 606/3 |
| 4,930,504 | 6/1990 | Diamantopoulos et al. ........... 606/3 X |
| 4,930,505 | 6/1990 | Hatje et al. ..................... 606/3 X |
| 4,931,053 | 6/1990 | L'Esperance, Jr. .............. 606/2 |
| 5,146,917 | 9/1992 | Wagnieres et al. ............... 606/17 X |
| 5,150,704 | 9/1992 | Tatebayashi et al. .............. 606/10 X |
| 5,259,380 | 11/1993 | Mendes et al. ................. 606/2 X |
| 5,337,741 | 8/1994 | Diamond ..................... 606/17 X |

FOREIGN PATENT DOCUMENTS

| | | |
|---|---|---|
| 3103731 | 5/1983 | Germany . |
| 3720742 | 1/1988 | Germany . |
| 245995 | 11/1969 | U.S.S.R. . |
| 741889 | 6/1980 | U.S.S.R. . |
| 993959 | 2/1983 | U.S.S.R. . |
| 114215A | 2/1985 | U.S.S.R. . |
| 1266540 | 10/1986 | U.S.S.R. . |

OTHER PUBLICATIONS

*Superantigens in Human Disease* by Johnson et al.
*Evidence for the Effects of a Superantigen in Rheumatoid Arthritis* by Pallard et al.
*Mendelian Inheritance in Man* by Victor A. McKusick, M.D.
*A Double Blind Study of Low Power Ha–Ne Laser Therapy in Rheumatoid Arthritis* by Oyamada . . . .

Primary Examiner—Stephen C. Pellegrino
Assistant Examiner—Michael Peffley
Attorney, Agent, or Firm—Allen, Dyer, Doppelt, Franjola & Milbrath

[57] ABSTRACT

An apparatus and method for irradiating an inflamed joint of a patient having rheumatoid or psoriatic arthritis are presented. A noncoherent source of radiation having a predetermined wavelength range is utilized to transilluminate affected tissues of the subject for a predetermined duration. The radiation source has sufficient intensity and is applied for sufficient duration to reducing inflammation and substantially halt disease progression.

5 Claims, 1 Drawing Sheet

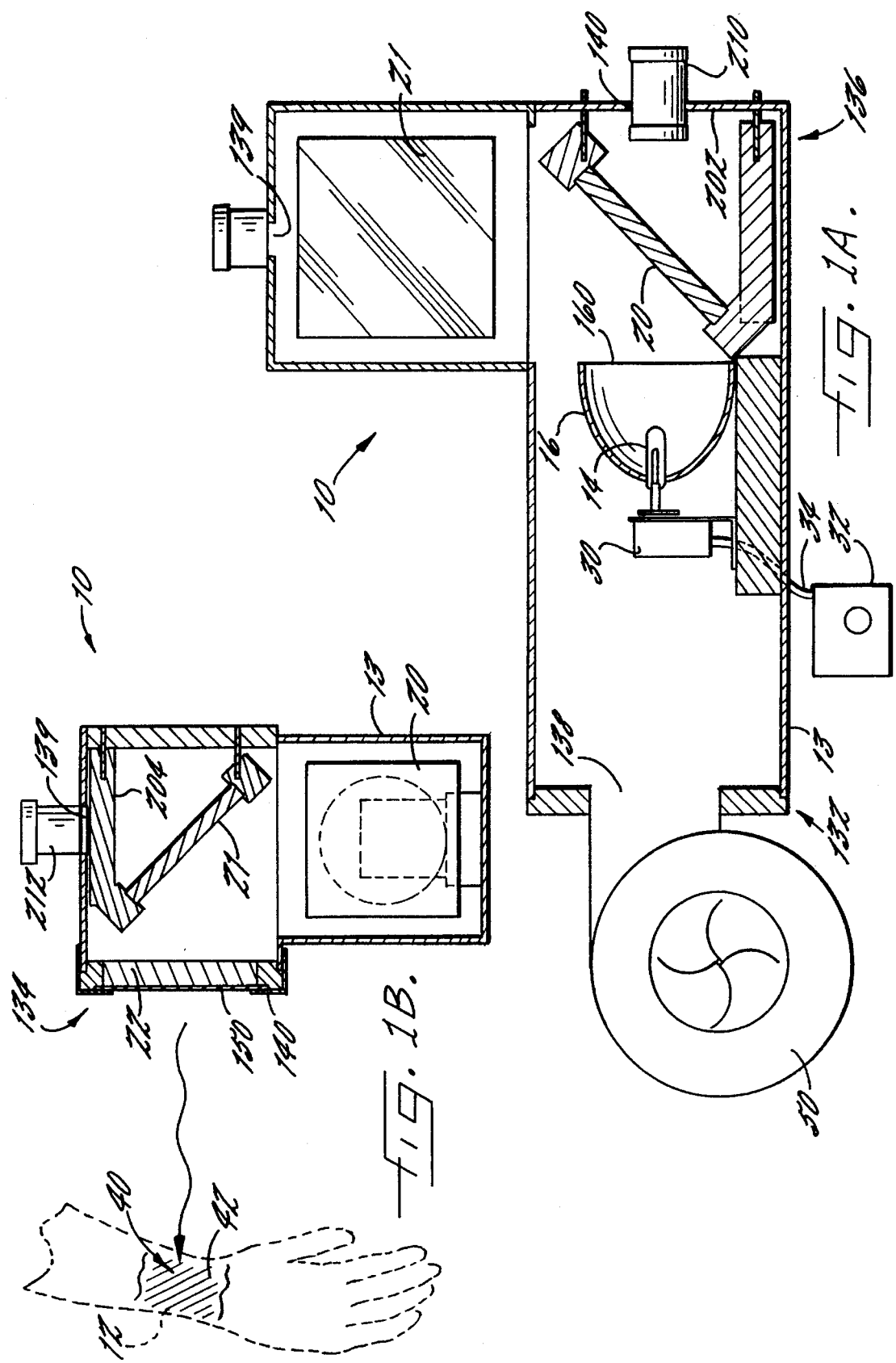

APPARATUS AND METHOD FOR TREATING RHEUMATOID AND PSORIATIC ARTHRITIS

This application is a continuation-in-part of applicant's application, Ser. No. 07/718,615, filed on Jun. 21, 1991, now U.S. Pat. No. 5,337,741 entitled *"Photo Radiation Treatment Apparatus and Method."*

BACKGROUND OF THE INVENTION

1. Field of the Invention

This invention relates to apparatus and methods for therapeutic intervention of the complex immune response in rheumatoid and psoriatic arthritis.

2. Background Summary

Arthritis is a general term that encompasses several distinguishable joint disorders, such as osteoarthritis, rheumatoid arthritis, ankylosing spondylitis, and psoriatic arthritis.

Osteoarthritis, also known as degenerative joint disease, is caused by long-term wear and tear on the protective cartilage that lines the inner surfaces of joints. Although typically a disorder of old age, certain predisposing conditions can hasten the degenerative process in younger persons. Symptoms may include joint aching and stiffness, with x rays showing a narrowing of the joint space and new bone formation adjacent to the joint. Treatment includes anti-inflammatory medication, heat, and physical therapy; in severe cases refractory to conservative treatment surgery, including joint replacement, may be necessary.

Rheumatoid arthritis (RA) is a chronic inflammatory condition that is believed to be an autoimmune disease, since an antibody, rheumatoid factor (RF), is present in the bloodstream of a majority of patients. The level of RF in the patient correlates with the severity of the disease. This antibody may be formed in response to an antigen that triggers a complex immune response, causing white blood cells and antibodies to infiltrate the synovial membranes. The resulting recurrent inflammation causes permanent damage to the joint cartilage, bones, ligaments, and tendons. Conventional wisdom suggests a genetic component that predisposes RA tendencies among Nordic, Celtic, and Slavic populations, and appears between the ages of 20 and 70, mostly in women. The symptoms include joint pain, aching, and stiffness, followed by joint swelling, redness, and warmth. Rheumatoid nodules may appear beneath the skin, especially around the elbow and sometimes the spine. Treatment usually consists of anti-inflammatory and immunosuppresant medication and short-term courses of asteroid such as prednisone. While these medications decrease joint inflammation, they do not alter the course of the disease. Remission-inducing and chemotherapy drugs are available for long-term use, but they are associated with potentially dangerous, even lethal, side effects. For instance, nonsteroidal anti-inflammatory drugs are know to cause digestive tract bleeding, and methodtrexate, an antineoplastic, can cause hepatotoxicity (liver cell damage) and pancytopenia (aplastic anemia). Artificial joint replacement is used in severe cases.

Ankylosing spondylitis (AS) is an inflammatory condition of the spine and sacroiliac joints. The hallmark of this disease is the bony fusion (ankylosis) of the spinal vertebrae, leading to permanent loss of flexibility of the back and neck. Other joints and tissues may also be affected by the inflammatory process. AS occurs most often in men between the ages of 20 and 40, and rarely is found after age 50. The cause of as is unknown, but a genetic predisposition is suspected. Pain and stiffness localized to the lower back and sacroiliac joints adjacent to the spine are the most common early manifestations, with arthritis in the hip, shoulder, or other joints also presenting. Gradually spinal immobility occurs, resulting in spinal deformity and decreased chest expansion. Treatment includes physical therapy and nonsteroidal anti-inflammatory medication, neither of which has a direct effect on the course of the disease.

Psoriatic arthritis, which is an arthritic condition associated with psoriasis, has similar symptoms to rheumatoid arthritis. While psoriasis and rheumatoid arthritis do indeed coexist in some patients, psoriatic arthritis is a distinct disease entity, with rheumatoid factor being absent. Treatment includes the use of salicylates and physical therapy, with adrenocorticosteroid drugs being administered as a last resort. Severe cases may be treated with immunosuppressants, which may be toxic. Severe psoriatic arthropathy not responsive to conventional antirheumatic therapy may be treated with methotrexate, although careful surveillance for evidence of myelosuppression, pancytopenia, and hepatotoxicity is required.

RELATED ART

Many devices that generate and project radiation transcutaneously have been used to treat arthritics, such as diathermy and laser devices. The transient anti-inflammatory action of induced hyperthermia is well established. Examples of these devices are disclosed in German Patent No. DE 3103731 A1, and Soviet Union Patent Publications SU 993959 and SU 741889. SU 993959 discloses the introduction of the antibiotic tetracycline into the subject's interarticular space and then irradiating the joint with a helium-neon laser for 2 to 4 minutes. SU 741889 teaches the introduction of dye material into the joint cavity and then an application of radiation from a 488-nm argon laser to the joint for 5 minutes. These techniques are palliative but do not result in a permanent remission of the disease, nor an arrest of its progression. In addition, these techniques require invasive procedures and hypodermic introduction of materials.

Other methods of providing palliation of arthritic symptoms are disclosed in Soviet Union Patent Publications SU 1266540 and SU 1142125A. These methods deliver thermal energy to the inflamed joint. No claim to prolonged remission or arrest of disease progression is made for these methods.

Kallenborn (U.S. Pat. No. 3,867,948) describes a method of delivering infrared radiation to the dermal layer of the skin, while cooling the epidermal layer with a fan. A possible use for the method includes cancer prevention, putatively by bioelectric means.

de Laforcade (U.S. Pat. No. 3,930,504) teaches the use of a light coagulator for the treatment of eye disorders such as diabetic retinopathy, in which case the beam is utilized to cauterize and reduce proliferation of blood vessels in front of the retina. The apparatus comprises a xenon arc lamp, a condenser, and a lens and diaphragms to converge the beam. The spectral characteristics of the xenon arc lamp are not elaborated, except to say that they approximate those of the sun. No rationale is given for the desirability of such a spectrum.

Laser photocoagulation for retinal applications is also the subject of Dewey's disclosure (U.S. Pat. No. 4,628,416). The apparatus is a variable-spot-size illuminator comprising a laser, lenses, and fiber optics, the arrangement of which permits maintaining total emitted energy while varying spot size focused on the retina. Spectral characteristics are neither disclosed nor taught as an important parameter.

Muller (U.S. Pat. No. 5,019,074) teaches an "erodible mask" for selective photoablation of soft tissue, specifically in ophthalmic applications. The apparatus is used to reprofile a cornea by providing a mask between the source and the cornea to control the radiation transmitted to the corneal surface. An argon fluoride laser, emitting at 193 nm, is the radiation source, with a saturation value not to be exceeded of 250 mJ per $cm^2$ per pulse.

Weissman et al. (U.S. Pat. No. 4,388,924) discloses the use of radiation, preferably from an argon ion laser, at a wavelength of 500 nm to destroy the root of a hair body, causing depilation. In practice, a short, high-energy pulse of light causes "sufficient heating of the hair root to destroy the blood vessels supplying the hair root."

The dual-wavelength laser scalpel of Menger (U.S. Pat. No. 4,791,927) utilizes coherent radiation at 300–350 and 500–800 nm to, respectively, cut and cauterize biological tissue.

Sinofsky (U.S. Pat. No. 5,071,417) teaches laser fusion of biological materials, such as in healing incisions and wounds or repairing blood vessels. In this application, solid-state lasers are preferred that emit in the range 1.4–2.5 μm.

A method and apparatus for achieving enhanced vascular growth is disclosed by L'Esperance (U.S. Pat. No. 4,931,053). This invention specifically requires coherent radiation, preferably in the form of a helium-neon, krypton, or diode laser emitting above 600 nm. Recommended energy delivery levels are in the range of 100–150 $\mu W/cm^2$. For the stated purpose of this invention, noncoherent radiation is specifically discounted, and photonoptical tissue breakdown is to be avoided.

SUMMARY OF THE INVENTION

Rheumatoid arthritis is believed to be caused by an antigenic particle, namely a viroid whose genetic material comprises an RNA strand. The disease was not documented prior to the seventeenth century AD, perhaps having been introduced into the human bloodstream via pre-Cambrian mining deposits. After introduction the viroid may be vertically transmitted, as a congenital disease, or contracted venereally or by inspiration. It is postulated that the viroid has dimensions of 8 nm by 720 nm and that it replicates opportunistically within the synovial fluid utilizing cell debris and autocatalysis.

The viroid's base sequence is recognized by the body's immune system to be an antigen, and thus the complex immune response is activated, including inflammation. Chronic inflammation leads to a proliferation of T lymphocytes and to the noted symptoms of joint erosion, cartilage loss, and other degenerative aspects.

Viroid particles are susceptible to photolysis, that is, structural breakup induced by radiation. It is believed that radiation of appropriate wavelengths such as are present in ambient light is capable of photolyzing the viroid, and that synovial fluid withdrawn from a patient under illuminated conditions will thus contain only fragments less than 200 nm in length, which resemble cell debris.

The theory behind the present invention holds that a noninvasive illumination of an affected joint at a wavelength at which the viroid particles are susceptible to photolysis, provided such wavelength will penetrate the skin layers, will lyse a sufficient portion of the viroids to eliminate the disease. It is to be emphasized that this is not intended to be a palliative treatment; rather, a lasting alleviation of symptoms is sought.

The method of the invention disclosed herein for the treatment of rheumatoid and psoriatic arthritis comprises irradiating the epidermal surface above an inflamed joint with a beam of noncoherent radiation having a wavelength in the range of 640–800 nm. The direction of the beam is preferably adjusted so that the transillumination of the intra-articular space containing synovial fluid is facilitated. The epidermal surface above the inflamed joint is preferably coated with mineral oil to facilitate penetration and minimize beam scattering. The incident power found most efficacious lies in the range of 40 to 200 $mW/cm^2$. The time of irradiation is approximately 20 minutes, using as an upper limit 150 $J/cm^2$ total exposure. The power density may be reduced at any time to avoid discomfort; the prescribed total energy dosage may then be administered by extending the exposure time proportionately, although such modulation is rarely required.

The apparatus of the invention comprises a source of radiation having an output wavelength between 640 and 800 nm, and means for directing the radiation at an inflamed joint of the subject. The power output of the radiation source is maintained at a sufficient level to photolyze the antigens believed responsible for evoking the complex immune response occurring within the inflamed joint of the subject.

An initial clinical trial indicated that an uncorrelated transient reduction of pain is experienced in nearly all subjects, attributed to local hyperthermia, with a typical duration of 3 to 6 hours. In a positive response, occurring within more than 70% of the population, the symptomatic indications of inflammatory processes subside within 12 to 48 hours following treatment, and a recurrence of symptoms is manifest between 18 and 36 months in over 80% of the responsive subjects. All subjects were medically diagnosed with rheumatoid arthritis, but not all titered positive for rheumatoid antibody (RA). It is therefore posited that some other disease entity may have been responsible for the failure to respond in the remaining fraction of the tested population. One subject had no recurrence of symptoms after 78 months to date without pharmacologic intervention. This subject had completed a course of prednisone and ibuprofen for 14 months prior to treatment and had an 18-year history of rheumatoid arthritis at that time.

A second clinical trial indicates that all subjects testing positive for the rheumatoid antibody responded with reduced inflammation, increased range of motion, and remission of pain. Four previously treated patients remained asymptomatic after 6 months without further intervention.

Of the entire test group of 33 in the second trial, positive response was reported for 23 subjects (70%), among which 10 were RA positive, 13 RA negative or had no RA test data. Negative response was reported for 10 subjects (30%), among which none was RA positive, 3 RA negative, and 7 had no RA test data.

It is believed that, although this test group were also all clinically diagnosed by their physicians with rheumatoid arthritis, another disease entity may be present in the group (e.g., chronic systemic candidiasis).

A control study was also undertaken, in which radiation restricted to wavelengths less than or equal to 550 nm and greater than or equal to 900 nm at 100 $mW/cm^2$ and 100 $J/cm^2$. The results of this test indicated that heat alone does not provide the long-lived therapeutic benefits reported for the 640–800 nm bandwidth.

It is thus an object of the present invention to provide an improved therapeutic modality #or treating rheumatoid and psoriatic arthritis.

It is another object to provide a method of treating rheumatoid and psoriatic arthritic inflammation by irradiating the epidermis of the subject with radiation having a wavelength bandwidth between 640 and 800 nanometers to transilluminate the arthritic joint with an incident power at a power and for a time sufficient to provide an effective treatment.

A further object of the invention is to arrest progressive degeneration caused by rheumatoid and psoriatic arthritis with a device that concentrates high-intensity electromagnetic radiation within a specific bandwidth upon the affected area of the patient.

Another object of the invention is to attenuate the body's complex immune response to antigens migrating through the synovial membrane and infiltrating adjacent soft tissues by transilluminating these structures with electromagnetic radiation having an effective wavelength bandwidth of 640–800 nm and photolyzing the antigen.

An additional object of the invention is to reduce pain, inflammation, and fluid-retention symptoms characterizing the complex immune response to rheumatoid and psoriatic arthritis.

Yet another object of the invention is to provide a prolonged reduction in the titer of the antigen disposed in the synovial fluid and adjacent tissues such that by using the therapeutic technique symptomatic relief of the disease may be extended for some months or years.

The features that characterize the invention, both as to organization and method of operation, together with further objects and advantages thereof, will be better understood from the following description used in conjunction with the accompanying drawing. It is to be expressly understood that the drawing is for the purpose of illustration and description and are not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWING

FIG. 1A AND 1B are cross-sectional views of the apparatus, comprising a tungsten source for generating radiation of the approximate blackbody color temperature of 3000K and means for filtering and directing the beam at the afflicted joint.

FIG. 1A is a side view; FIG. 1B is an end view.

DETAILED DESCRIPTION OF THE PREFERRED EMBODIMENT

The preferred embodiment of the present invention will now be described with reference to FIGS. 1A and B.

DESCRIPTION OF THE APPARATUS

The apparatus of the present invention, referred to generally by 10, is illustrated in FIGS. 1A and B. Apparatus 10 produces high-intensity noncoherent electromagnetic radiation directed at an epidermal surface 12 above an inflamed joint 40 of a subject to reduce inflammation caused by rheumatoid or psoriatic arthritis.

Apparatus 10 in the preferred embodiment includes an L-shaped aluminum housing 13 having an upstream end 132 at the end of one arm of the "L," a downstream end 134 at the end of the other arm of the "L," and a central portion 136 at the junction of the two arms of the "L." Upstream end 132 has an aperture 138 therein, and downstream end 134 has an aperture 139 therein, and central portion 136 has an aperture 140 therein opposed to aperture 138. On the inside surface of central portion 136 opposite upstream end 132 is a light-absorbing flat-black backplate 202 and an externally mounted black alodized aluminum heat sink 210. Similarly, on the inside surface of downstream end 134 is another light-absorbing flat-black backplate 204, and another externally mounted black alodized aluminum heat sink 212. On the inside of the "L," perpendicular to downstream end 134, is wall 140, in which is exit aperture 150.

Housing 13 contains a radiation source 14, approximately midway between upstream end 132 and central portion 136, powered by an infinitely adjustable 15–30 V ac, 8 A power supply 30 (M. Trautman, Thonatosassa, Fla.). Radiation source 14 in the preferred embodiment is a Philips tungsten/halogen lamp rated for 200 W, 30 V, and 5150 lumens (Philips DCR6.6A) disposed within housing 13. Although a tungsten source is preferred, any source that provides radiation in the range of at least 640–800 nm, the preferred bandwidth, is acceptable.

Tungsten radiation source 14 is enabled, adjusted, and disabled by switch triac 32, which is situated outside housing 13, connected to power supply 30 by lead 34.

Source 14 is cooled by blower 50, affixed at upstream end 132 outside housing 13 and positioned to provide an airstream through aperture 138 to impinge upon source 14 and other internal components, and exits through apertures 139 and 140.

Ellipsoidal reflector 16 (24K gold plated, Skytrackers of America, Inc., Temecula, Calif., Model EA-8) is configured to project a converging beam to a spot 90 mm beyond the exit rim 160 of the reflector. Reflector 16 surrounds source 14 and opens toward the central portion 136 of apparatus 10.

Reflector 20 is positioned inside housing 13 at the central portion 136 at 45 degrees to the converging beam from reflector 16. Reflector 21 is positioned inside housing 13 at the downstream end 134 of housing 13, is rotated 90 degrees from the plane of reflector 20, and is at 45 degrees to aperture 139. Both reflectors 20 and 21 in the preferred embodiment are modified quarter-wave Fabry-Perot multilayered stacks having Melles-Griot/281 coating on a 10-mm-thick borosilicate substrate. They are both 65×90 mm and are custom manufactured to specification by Melles-Griot (Irvine, Calif.).

At downstream end 134 is affixed low-pass filter 22, adjacent wall 140 and covering exit aperture 150, in the preferred embodiment a Schott RG-645 glass filter, 5 mm thick and 100 mm in diameter (fabricated to order by Precision Glass and Optics, Santa Ana, Calif.).

All the optical components, source 14, ellipsoidal reflector 16, reflectors 20 and 21, and low-pass filter 22, are affixed via fastening means to housing 13.

The desired output beam is generated with the use of the above-described apparatus 13 as follows: Tungsten source 14 is brought up to the normal operating range of 200 W. The ellipsoidal reflector 16 captures 80% of the projected flux in the design bandwidth and projects a converging beam to a spot 90 mm beyond the exit rim 160 of reflector 16.

The converging beam is intercepted by reflector 20, which selectively reflects and transmits wavelengths of the beam, the transmitted portion of which is projected to the light-absorbing backplate 202. Since the beam is converging, the incident angle varies from 20 to 70 degrees. This shifts the reflectance curve of the reflector stack approximately plus or minus 30 nm of the published (45 degree) curve, depending on the location of the impinging beam.

The reflected beam converges to a point half-way to reflector 21, impinging on reflector 21 as a diverging beam, whereupon another wavelength-selective reflectance directs the beam toward low-pass filter 22, in the same manner as for reflector 20.

The low-pass filter 22 then absorbs the shorter wavelengths and passes the longer wavelengths with an internal transmittance efficiency greater than 91%, with a sharp cutoff at 645 nm.

It should be pointed out that the right-angle rotation of reflectors 20 and 21 relative to each other achieves three optical consequences important to the Q of the output bandwidth:

(1) The reflectance at the center of the bandwidth, plus or minus 50 nm, is better than 99%.

(2) The adjacent sidebands are attenuated by the effects of bandwidth shift, since the beam having large angular deviations from 45 degrees on reflector 20 strike reflector 21 more nearly at 45 degrees, and similarly, those beams in the plane more nearly at 45 degrees incidence on reflector 20 impinge at greater or lesser angles on reflector 21.

(3) Beyond the nominal bandwidth, the attenuation of the sidebands is markedly enhanced by the transposition of the S and P planes of the mirrors, which multiple reflectance tends to attenuate by juxtaposition of the S or P plane peaks with the P or S plane troughs of the other mirror.

As a consequence of selection of reflectant filtration as the primary mode of wavelength separation, a high system efficiency is achieved in transmission of the desired bandwidth.

DESCRIPTION OF THE METHOD

The preferred embodiment of the method comprises irradiating the epidermal surface transverse to an inflamed joint. The irradiation, preferably between 640 and 800 nm, is applied with an incident power of 40–200 mW/cm$^2$ for a period of approximately 20 min. It has been found that these values are sufficient to reduce or completely eliminate the arthritic inflammation.

On a clear day the incident power from noontime sun is typically in the range of 110–130 mW/cm$^2$. As this is in the same range as the incident power called for in the method of the present invention, it may be argued that the efficacy of the method is not attributable to local heating of the inflamed joint.

In the preferred embodiment of the method the epidermis 12 above the inflamed joint 40 to be treated is coated with mineral oil 42 prior to irradiation. The mineral oil enhances subcutaneous transmission of the beam, permitting more energy to be delivered to deep tissues.

The following examples of clinical results indicate the efficacy of the treatment embodied in the present invention:

EXAMPLE 1

Subject is a 59-year-old white male having RA immunoglobulin positive for 4 years and was symptomatic for 17 years. The principal source of inflammation was in the symmetrical proximal carpals and metacarpals and phalanges-metatarsals. He had been taking aspirin for relief of pain and inflammation.

The subject was initially dosed with 200 joules on the palmar and dorsal right first metacarpus. On the following day the subject reported a remission of inflammation with a return of range of motion of the irradiated joints without pain.

Three days later 200 joules were irradiated at the palmar and dorsal as well as the left first metacarpus. A remission of inflammation was recorded the following day with a return of normal range of motion without pain of the irradiated joints.

The next day the palmar and dorsal surfaces were irradiated as well as the left second metacarpal and left proximal phalange with 100 joules. The following day the subject reported a reduction of inflammation and pain of the irradiated joints.

Two days later the subject was irradiated with 200 joules on the palmar and dorsal, the left second metacarpal and the left second proximal phalange. The subject experienced remission of inflammation the following day.

The next day the subject was irradiated with 200 joules palmar and dorsal on the remaining metacarpals and phalanges. The subject experienced overnight remission of inflammation and pain.

One month later the right plantar and dorsal metatarsals and proximal phalanges were irradiated with 1200 joules on each surface for a total of 4800 joules. The subject experienced a remission of inflammation and pain.

On the following day the left plantar and dorsal and metatarsals and proximal phalanges were radiated with 1000 joules on each surface for a total of 4000 joules. A remission of inflammation and pain was reported by the subject.

Approximately 1 year later the subject reported symmetrical recurrence of pain and inflammation in the first metacarpals. The subject was irradiated on the metacarpals and proximal phalanges en bloc for a total of 6000 joules. Subject reported a positive response as there was a remission of inflammation and pain.

A year and a half later the subject reported symmetrical recurrence of pain and inflammation in metatarsals. The subject was irradiated on the metatarsals on proximal phalanges, as well as the left plantar and dorsal, with a dosage of 1000 joules on each surface. Subject reported a remission of inflammation and pain. Subject has not reported a recurrence as of date.

Subsequent treatment of the neck, shoulders, wrists, and knees produced a remission that continues to the present time. The use of aspirin was discontinued.

EXAMPLE 2

The subject is a 20-year-old white male having RA immunoglobulin positive, with an 18-year history of RA. The inflammation on the subject included the tarsals and metatarsals on the right foot. The subject was irradiated on the right foot with 6000 joules total.

The subject reported overnight remission of inflammation and pain. Annual followups relate continuing remission of symptoms as of date 6 years later. Within 24 hours of treatment the swelling had subsided, and full range of movement was restored to both ankles. The use of anti-inflammatory medication was discontinued, and remission has continued to the present since the March, 1987 treatment.

EXAMPLE 3

The subject is a 39-year-old black female experiencing RA immunoglobulin positive for the past 9 years. The left scapula, left femoral head and pelvis were irradiated with a dosage of 2400 joules each. Subject experienced a positive response where the inflammation and pain were remitted.

Four days later the left humerus head, right and left tarsus, first wrist, and second and third metacarpals were irradiated with 2000, 2400, and 1400 joules, respectively. The subject experienced a positive response where a remission of inflammation and pain were recorded.

A year and a quarter later the subject reported recurrence in the left hip. The subject is treated with irradiation on the left scapula, left femoral head, and pelvis. The dosage of the radiation was increased to 4800 joules, and the subject experienced a positive response. In this response the pain and the inflammation were decreased.

One year later the subject reported no recurrence.

EXAMPLE 4

The subject is a 20-year-old white male, experiencing ankylosing spondylitis. A dosage of 2400 joules was applied to the lumbar-sacral spine. No response was obtained.

In this instance, it was demonstrated that ankylosing spondylitis was not arrested with radiation. This example also implies rheumatoid arthritis is arrested due to photolyzing antigens, and not due to thermal effects.

EXAMPLE 5

The subject is a 4-year-old juvenile with arthritic symptoms in the right tarsus. Two doses at 4-day intervals at 900 joules were applied to the subject's right tarsus. The subject did not respond to the irradiation application.

This example suggests that juvenile arthritis is not the same disease entity as adult rheumatoid arthritis.

EXAMPLE 6

A subject having osteoarthritis, age 60, in the distal phalanges. A dosage of 400 joules was applied to the phalanges. Subject did not respond to this application.

This example demonstrated that osteoarthritis is a disease entity of differing causality. This example also demonstrated that treating osteoarthritis by transilluminating electromagnetic radiation does not provide long-term reduction of pain and inflammation.

EXAMPLE 7

A 62-year-old female having rheumatoid arthritis on the wrists and the hands was irradiated en bloc in four exposures. The palmar and ventral surfaces were irradiated with a dosage of 2400 joules each. The subject experienced a positive response in metacarpals and a partial response in wrists.

Less than 1 month later the wrists of the subject were irradiated with 3000 joules. The subject had a positive response, a reduction of pain and inflammation.

Less than 2 years later the subject was observed and a symptomatic recurrence was reported. The subject was retreated with a 3000 joules application. A positive response was reported by the subject with a reduction in pain and inflammation.

EXAMPLE 8

The subject is a 54-year-old male and was diagnosed as rheumatoid in the knuckles, shoulders, elbows, knees, ankles and toes.

The subject was treated on the knuckles of the right hand with a 30-minute exposure. The subject had no pain or stiffness by the following morning, although inflammation was still present in the hands.

One week later the knuckles of the left hand were exposed for approximately 15 minutes on each side, and the toes of the right foot were also exposed for 15 minutes. The dosage applied was 1800 joules.

The following morning the subject experienced no pain or stiffness in the right foot while the subject's untreated left foot was throbbing. The subject did not experience any pain but did have some stiffness in the untreated left hand. The previously treated right hand felt normal with no discomfort of any kind. Subject did experience pain and swelling for a few days after heavy impact to the right hand during physical activity with a target pistol.

Three weeks later the subject's knuckles of the right hand were treated, and 2 weeks following that treatment, the knuckles of the left hand as well as the toes of the right foot were treated. In both cases the subject was treated for a duration of 20 minutes at a dosage rate of 1800 joules.

One month later all the areas that were treated were normal. Subject did not experience stiffness or discomfort.

Two months after the last treatment the subject was exposed on his heel of the right foot for approximately 20 minutes with a dosage level of 1800 joules. Subject experienced an immediate relief of pain. The following day the subject experienced less pain with no stiffness in the right heel. Knuckles in the right hand, treated the previous month, felt normal with no discomfort of any kind, and the knuckles of the left hand and toes of the right foot, treated 2 months previously, felt normal with no discomfort of any kind.

EXAMPLE 9

Subject is a 60-year-old female who was diagnosed with rheumatoid arthritis in 1982. The primary inflammation sites were in the hands, with lateral drifting presenting in both hands.

Within 24 hours of treatment (in 1988) the subject experienced normalization of skin temperature and reduction of joint pain and tenderness at the treated site. Within 96 hours of treatment the subject reported an increased range of motion, reduction of swelling and inflammation, and a substantial reduction of joint pain and stiffness at the treated site. The lateral drifting of the hands upon extension ceased. The left hand returned to its normal extension, and the right, which was reported to have a permanent drift prior to treatment, did not degenerate any further since therapy.

Subsequent treatment of the subject's hands 2 years later produced similar results, with substantial reduction of symptoms continuing for over a year.

EXAMPLE 10

Subject is a 62-year-old male who was diagnosed with rheumatoid arthritis in 1977. He had been taking prednisone during acute episodes and Feldene daily to reduce inflammation.

Subject was irradiated in 1988 in the thumb and wrist on both sides and the left ankle, with resulting pain abatement and increased flexibility.

Retreatment has occurred at intervals of 15 months initially and more recently at intervals of 12 months, providing overnight and sustained relief from pain and stiffness between treatments. The progression of the disease has, in subject's opinion, slowed or halted.

EXAMPLE 11

Subject is a 32-year-old female having been diagnosed with rheumatoid arthritis in 1989 who had been taking ibuprofen for pain and inflammation.

Within 24 hours of treatment in 1989 subject reported increased range of motion, substantial reduction of joint pain and tenderness, increased strength in the hands, and decreased swelling. Within 96 hours complete recovery was reported, with no pain, swelling, loss of strength, or tenderness. Retreatment in 1992 produced the same results. Remission of the symptoms continues to the present time. The use of ibuprofen has been discontinued.

EXAMPLE 12

Subject is a 43-year-old male who had been taking methotrexate, gold shots, and Plaquenil(TM) for inflammation.

Treatment was performed on the hands, feet, ankles, shoulders, elbows, knees, and hips in 1991. Within 24 hours of treatment reduction of swelling and inflammation was reported, as well as a normalization of skin temperature and a substantial reduction of joint pain at the treated site. Additional improvements continued within 96 hours of treatment. Substantial reduction of symptoms continued for 12 months, at which time retreatment gave similar results. The use of methotrexate, gold shots, and Plaquenil(TM) was discontinued.

EXAMPLE 13

Subject is a 73-year-old female testing positive for rheumatoid antibody, having been diagnosed 4 years previously with rheumatoid arthritis. Prednisone had been prescribed but had been discontinued, with only ibuprofen being taken at the time of treatment.

The left and right hands were treated, specifically, the dorsal aspects of the right and left carpus, metacarpus, and proximal phalanges, at 40 J/cm$^2$. A reduction in inflammation and pain and an increased range of motion were reported. The right and left tarsus were treated, with resulting remission of pain and tenderness. Prescription drug use has been discontinued.

EXAMPLE 14

Subject is a 72-year-old female, diagnosed RA positive, having lateral drift of the hands, hypothermic fingers, and nonclosable fist.

A first treatment of 40 J/cm$^2$ to the palmar and distal metacarpals and proximal phalanges of the left hand resulted in decreased soreness, increased range of motion and strength, and improved circulation.

Treatment of the right metacarpal, palmar, and dorsal aspects resulted in improvement, although less than in the left hand.

Additional treatment of the left hand caused an increase in range of motion from 5 degrees to approximately 15 degrees at the wrist.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A method of treating an inflamed joint of a patient having rheumatoid or psoriatic arthritis, comprising the steps of:

providing a source of noncoherent radiation having an output wavelength between 640 and 800 nm and an incident power of 40 to 200 mW/cm$^2$; and irradiating an epidermal surface transversely to transilluminate the inflamed joint with the radiation for a time sufficient to reduce the inflammation of the joint, the time generally in the range of 10 to 20 minutes.

2. The method recited in claim 1, further comprising:

facilitating penetration of the radiation by coating the epidermal surface with mineral oil prior to irradiating the epidermal surface.

3. A method of treating an inflamed joint of a patient having rheumatoid or psoriatic arthritis, comprising the steps of:

providing a source of radiation and optical means that produces first a converging, then a diverging, beam with a predetermined bandwidth that includes a wavelength range of 640 to 800 nm;

filtering all wavelengths in the convergent, then divergent, beam that lie outside the wavelength range;

directing the filtered beam at an epidermal surface transverse to the inflamed joint; and reducing the joint inflammation by irradiating the inflamed joint with the filtered beam with an incident power of 40 to 200 mW/cm$^2$ to reduce the inflammation, the irradiation presenting the epidermal surface with a total incident energy.

4. The method recited in claim 3, further comprising:

limiting the total incident energy of the radiation to 150 J/cm$^2$.

5. A method of treating rheumatoid and psoriatic arthritic inflammation in the body of a subject, the method comprising the steps of:

providing a radiation source that produces first a converging, then a diverging beam with wavelengths having a bandwidth in the range of 640 to 800 nanometers;

converging the beam;

filtering all wavelengths outside the wavelength bandwidth while the beam is converging then diverging;

directing the filtered radiation at the epidermis of the subject adjacent the arthritic inflammation; and reducing the arthritic inflammation by maintaining the radiation output at an incident power on the order of between about 40 to 200 milliwatts per square centimeter for a time sufficient to provide an effective treatment but not to exceed 150 joules per square centimeter when the output of the radiation source transilluminates the affected soft tissues.

* * * * *